(12) United States Patent
Hipp et al.

(10) Patent No.: US 8,057,415 B2
(45) Date of Patent: Nov. 15, 2011

(54) TRAUMA CERVICAL STABILITY DEVICE AND METHODS OF USING SAME FOR DIAGNOSTIC PURPOSES

(75) Inventors: John A. Hipp, Manvel, TX (US); Peleg Ben-Galim, Houston, TX (US); Nachum Borivker, Jerusalem, IL (US); Yakov Dashevsky, Jerusalem, IL (US); Barak Tzachar, Petach Tikva, IL (US)

(73) Assignee: Baylor College of Medicine, Houston, TX (US)

( * ) Notice: Subject to any disclaimer, the term of this patent is extended or adjusted under 35 U.S.C. 154(b) by 0 days.

(21) Appl. No.: 12/840,387

(22) Filed: Jul. 21, 2010

(65) Prior Publication Data

US 2010/0286581 A1    Nov. 11, 2010

Related U.S. Application Data

(63) Continuation-in-part of application No. 12/009,653, filed on Jan. 22, 2008, now abandoned.

(51) Int. Cl.
*A61F 5/00* (2006.01)
*A42B 1/06* (2006.01)

(52) U.S. Cl. ............................ 602/18; 2/410
(58) Field of Classification Search .................... 602/18, 602/17, 12, 5, 1; 2/425, 2, 410, 411, 415, 2/416, 418, 421
See application file for complete search history.

(56) References Cited

U.S. PATENT DOCUMENTS

| | | | |
|---|---|---|---|
| 2,102,069 A | 12/1937 | Hanicke | |
| 2,474,200 A | 6/1949 | McBee | |
| 2,807,260 A | 9/1957 | Teufel | |
| 2,820,455 A | 1/1958 | Hall | |
| 2,904,040 A | 9/1959 | Hale | |
| 3,134,106 A | 5/1964 | Shaffer | |
| 3,507,273 A | 4/1970 | Yellin | |
| 3,601,123 A | 8/1971 | McFarland | |
| 3,724,452 A | 4/1973 | Nitschke | |
| 3,776,224 A | 12/1973 | McFarland | |

(Continued)

FOREIGN PATENT DOCUMENTS

DE         29918767         5/2000

(Continued)

OTHER PUBLICATIONS

International Preliminary Report on Patentability published Jul. 27, 2010 for PCT/US09/00375 filed Jan. 22, 2009.

(Continued)

*Primary Examiner* — Patricia Bianco
*Assistant Examiner* — Tarla Patel

(57) ABSTRACT

Trauma cervical stability devices for use by ambulatory personnel arriving at the scene of an injured patient are disclosed. The trauma cervical stability devices comprise a cap element, releasable and adjustable head straps, a shoulder harness, and at least one adjustable member operatively connected to the cap element and the shoulder harness. The trauma cervical stability devices are compact, easy to use, inexpensive to manufacture, and can be placed on a patient with little or no movement of the patient. The trauma cervical stability devices are also useful in diagnosing the severity of damage to a neck and the stability of the patient's neck by applying forces to the patient's head using the trauma cervical stability device. In another embodiment of the devices the devices comprise head straps 210, shoulder harnesses 220, lateral head elements 212, and adjustable pressure fixation elements 214. The fixation elements may be vacuum pillows.

18 Claims, 11 Drawing Sheets

U.S. PATENT DOCUMENTS

| | | | |
|---|---|---|---|
| 3,795,243 | A | 3/1974 | Miller |
| 3,957,040 | A | 5/1976 | Calabrese |
| 4,219,193 | A | 8/1980 | Newman |
| 4,677,969 | A | 7/1987 | Calabrese |
| 4,793,334 | A | 12/1988 | McGuinnes |
| 5,088,482 | A | 2/1992 | McGuinnes |
| 5,123,408 | A | 6/1992 | Gaines |
| 5,195,947 | A | 3/1993 | Bode |
| 5,272,770 | A | 12/1993 | Allen |
| 5,302,170 | A | 4/1994 | Tweardy |
| 5,336,139 | A | 8/1994 | Miller |
| 5,371,905 | A | 12/1994 | Keim |
| 5,385,535 | A | 1/1995 | McGuinness |
| 5,433,696 | A | 7/1995 | Osti |
| 5,531,669 | A | 7/1996 | Varnau |
| 5,581,820 | A | 12/1996 | Cartwright et al. |
| 5,624,387 | A | 4/1997 | McGuinnes |
| 6,267,741 | B1 | 7/2001 | Lerman |
| 6,368,295 | B1 * | 4/2002 | Lerman ............... 602/17 |
| 6,740,055 | B2 | 5/2004 | Dominguez |
| 6,899,690 | B2 | 5/2005 | Saunders |
| 6,968,576 | B2 * | 11/2005 | McNeil et al. ............ 2/425 |
| 7,128,724 | B2 | 10/2006 | Marsh |
| 7,430,767 | B2 | 10/2008 | Nagely |
| 2001/0047143 | A1 | 11/2001 | Meyer |
| 2007/0156071 | A1 | 7/2007 | Cojbasic |
| 2008/0139984 | A1 | 6/2008 | Tranfic |
| 2009/0187129 | A1 | 7/2009 | Ben-Galim |

FOREIGN PATENT DOCUMENTS

| | | |
|---|---|---|
| WO | 2007020481 | 2/2007 |
| WO | 2009/094147 | 7/2009 |

OTHER PUBLICATIONS

Written Opinion published Jul. 22, 2010 for PCT/US09/00375 filed Jan. 22, 2009.

International Search Report published Jul. 30, 2009 for PCT/US09/00375 filed Jan. 22, 2009.

Notification of Transmittal of the International Search Report and Written Opinion of the International Searching Authority, or the Declaration, Apr. 2, 2009, pp. 1-3, PCT/US2009/000375, European Patent Office.

International Search Report, Apr. 2, 2009, pp. 1-6, PCT/US2009/000375, European Patent Office.

Written Opinion of the International Searching Authority, or the Declaration, Apr. 2, 2009, pp. 1-6, PCT/US2009/000375, European Patent Office.

Becker Orthopedic, Becker Orthopedic Company History/Catalog, 2005, pp. 1-134, Becker Orthopedic Appliance Co., USA.

* cited by examiner

TRAUMA CERVICAL STABILITY DEVICE AND METHODS OF USING SAME FOR DIAGNOSTIC PURPOSES

CROSS REFERENCE TO RELATED APPLICATIONS

The present application is a continuation-in-part application of U.S. patent application Ser. No. 12/009,653, filed Jan. 22, 2008, and claims priority therefrom.

BACKGROUND

1. Field of Invention

The invention is directed to trauma cervical stability devices and, in particular, to adjustable cervical stability devices capable of easy and cost effective use by ambulatory personnel at the scene of the injury and of allowing injury diagnosis upon arrival at the hospital.

2. Description of Art

Trauma cervical collars are generally known in the art. Briefly, these cervical collars are carried on ambulances and other emergency personnel vehicles and are usually one-time use devices. These cervical collars provide limited, if any, means to adjust the cervical collar to fit the patient while securing the cervical collar to the injured patient. Generally, the patient must be moved to secure the cervical collar to the patient. Movement of the patient, however, can cause additional injury to the patient. In those cervical collars where adjustment is provided, the adjustment capabilities are limited which can result in the patient's head not being sufficiently stabilized with respect to the patient's spine, neck, or body.

In other cervical collars, adjustment of the cervical collar may be achieved without excessive movement of the patient, however, the cervical collar is large and complex. Thus, these cervical collars are not only difficult to store in emergency vehicles where space is limited, they are difficult to use by emergency personnel. Accordingly, these types of devices instead are used to rehabilitate the patient's injured neck, e.g., after diagnosis and, generally, operation on the patient at a hospital, as opposed to stability a traumatic injury to a patient at the scene of the injury.

SUMMARY OF INVENTION

Trauma cervical stability devices for using by ambulatory personnel arriving at the scene of an injured patient are disclosed. Broadly, the trauma cervical stability devices comprise a cap element, releasable and adjustable head straps, a shoulder harness, and at least one adjustable member operatively connected to the cap element and the shoulder harness.

In another embodiment of the invention there is provided a trauma cervical stability device which includes a pair of shoulder harnesses, a pair of lateral head elements and a pair of adjustable pressure fixation elements. When the pressure fixation elements are evacuated and in their rigid mode they support and fix the neck and head of the patient so that there is no movement of the head relative to the torso of the patient. The head and torso are fixed in their instant relative disposition that is in the relation between them when found by a first responder. Head straps, shoulder harness straps, and optionally waist straps further secure the device to the patient.

The trauma cervical stability devices are compact, easy to use, inexpensive to manufacture, and can be placed on a patient with little or no movement of the patient. The trauma cervical stability devices are also useful in diagnosing the severity of damage to a neck and the stability of the patient's neck by applying forces to the patient's head using the trauma cervical stability device. It is to be understood, however, that the effects and results of the trauma cervical stability devices disclosed herein are dependent upon the skill and training of the operators and surgeons.

While the invention will be described in connection with the preferred embodiments, it will be understood that it is not intended to limit the invention to that embodiment. On the contrary, it is intended to cover all alternatives, modifications, and equivalents, as may be included within the spirit and scope of the invention as defined by the appended claims.

DETAILED DESCRIPTION OF INVENTION

Figure 1:
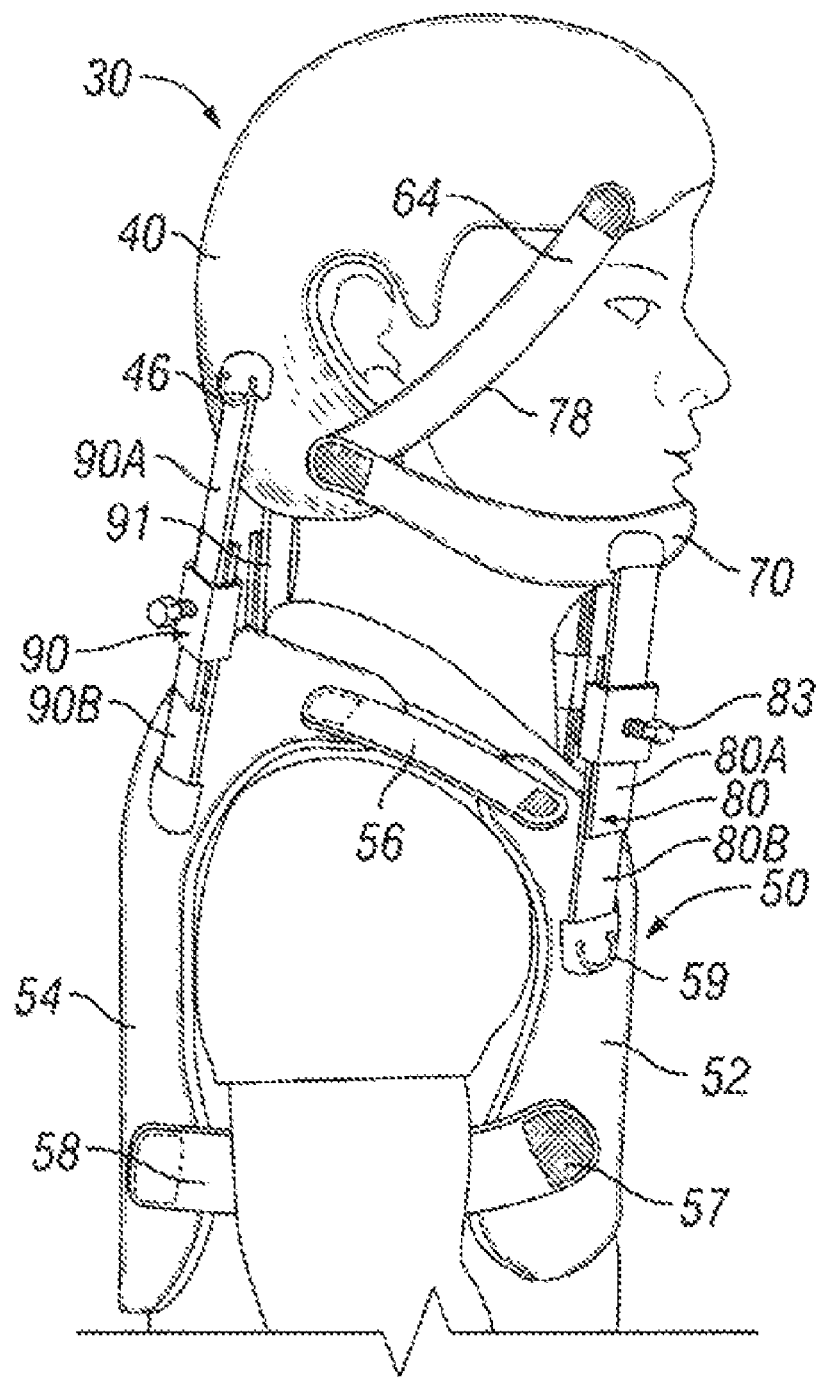
FIG. 1 is a perspective view of one embodiment of the trauma cervical stability device disclosed herein shown secured to a patient.
Figure 2:
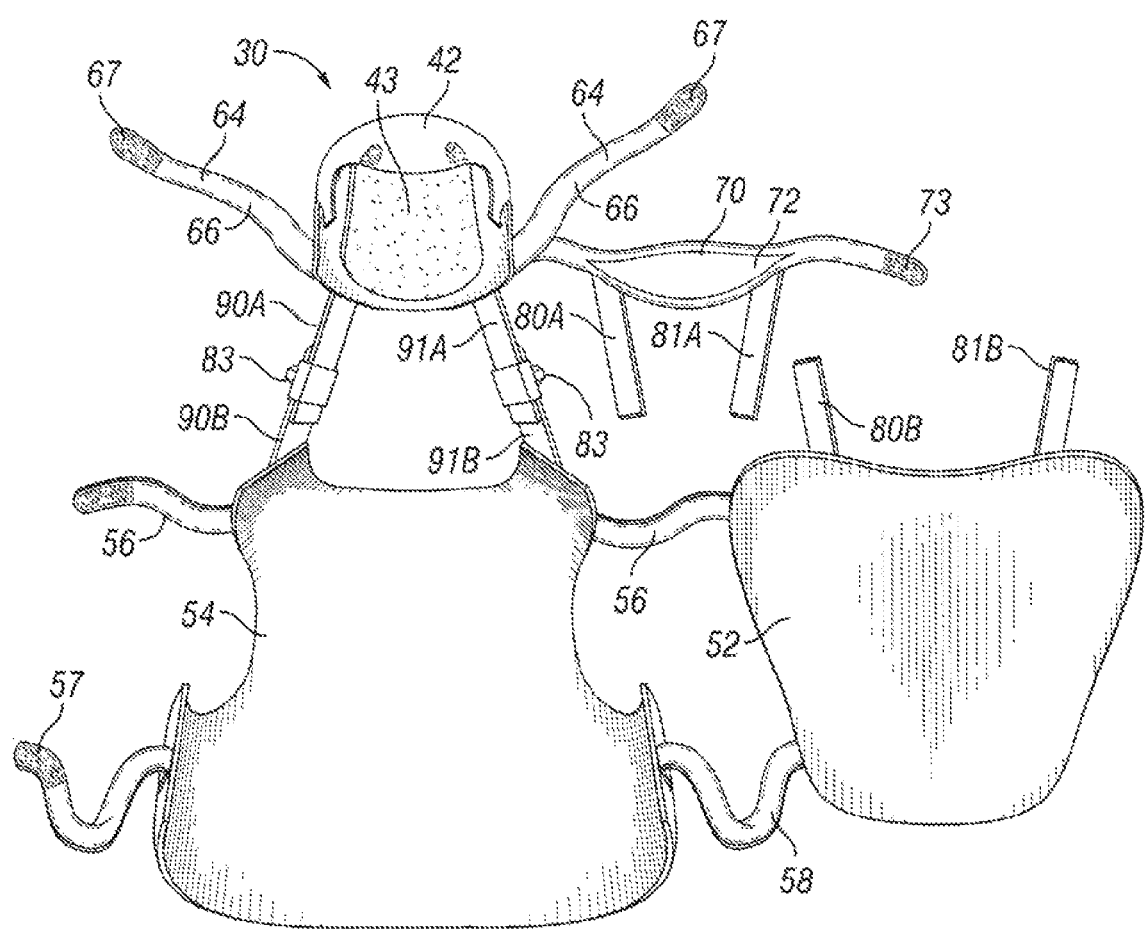
FIG. 2 is a perspective view of the trauma cervical stability device shown in FIG. 1 illustrated in the flat position before being secured to a patient.

Referring now to FIGS. 1-2, in one embodiment, trauma cervical stability device 30 includes cap element 40, shoulder harness 50, head strap 64, chin strap 70, anterior adjustable members 80, 81 and posterior adjustable members 90, 91. Cap element 40 comprises an inner wall surface 42 (FIG. 2) shaped for receiving the head of a person or patient. Cap element 40 may be formed from any suitable material that provides rigidity, such as plastic materials. As shown in FIG. 2, inner wall surface 42 includes a cushion material 43, such as foam, so that inner wall surface 42 can conform to the contour of the patient's head.

Cap element 40 covers the posterior and crown or top portions of the head of the patient. In the embodiment shown in FIGS. 1-2, cap element 40 covers not only the posterior and crown portions of the head of the patient, but also extends over the forehead of the patient. Although cap element 40 is shown in the embodiment of FIGS. 1-2 as being formed of a single piece of material, it is to be understood that cap element 40 may be formed by two or more separate pieces such as in the embodiment of FIGS. 4-7.

Due to cap element 40 covering the posterior surface of the patient's head as well as a at least a portion of the frontal lobe of the patient's head, which, in some embodiments also includes covering a portion of the forehead of the patient, when cap element 40 is connected to shoulder harness 50 as discussed in greater detail below, a downward force is applied to the head of the patient to assist in stabilizing the head of the patient relative to the body of the patient. The term "downward force" is used herein to describe forces applied in the direction of from the top of the head to the body and includes forces applied straight down toward the body, e.g., at a vertical angle (i.e., at a right angle to the horizon), as well as at an angle other than a vertical angle, e.g., at a 45 degree angle, a 30 degree angle, a 10 degree angle, an 80 degree angle, to the vertical angle.

Shoulder harness 50 includes front or breast plate 52 and back plate 54. One or both of breast plate 52 and back plate 54 includes inner wall surfaces having a cushion for conforming to the shape of the patient's body to support and comfort the patient's body. In one embodiment, both breast plate 52 and back plate 54 are formed from a rigid material, such as plastic, having a foam insert secured to the inner wall surface of the breast plate 52 and back plate 54. Shoulder straps 56 and body straps 58 releasably secure breast plate 52 with back plate 54. In the embodiment shown in FIGS. 1-2, shoulder straps 56 and body straps 58 include Velcro® pads 57 to releasably secure breast plate 52 to back plate 54.

Head strap 64 and chin strap 70 include a soft, cushioned inner wall surfaces 66, 72, respectively for conforming to and/or providing comfort to, the patient's head and chin. Head strap 64 and chin strap 70 are releasably secured to cap element 40. In the embodiment shown in FIGS. 1-2, head strap 64 and chin strap 70 include Velcro® pads 67, 73 to releasably secure head strap 64 and chin strap 70 to cap element 40.

Anterior adjustable members 80, 81 are secured at their upper and lower ends to chin strap 70 and breast plate 52, respectively. In one embodiment, anterior adjustable members 80, 81 are secured at their upper and lower ends to chin strap 70 and breast plate 52 respectively by rotatable members (not shown) to allow the connections between the upper and lower ends of anterior adjustable members 80, 81 to chin strap 70 and breast plate 52, respectively, to pivot and rotate so that the angle of intersection between anterior adjustable members 80, 81 chin strap 70 and breast plate 52 can be adjusted. Suitable rotatable members include, but are not limited to, lockable ball and socket connections so that the connections can pivot to the desired orientation and locked in place. Alternatively, only one of the connections between anterior adjustable members 80, 81 and chin strap 70 or breast plate 52 is rotatable, so that the other connection is fixed, i.e., the angle of intersection between anterior adjustable members 80, 81 and chin strap 70 or breast plate 52 cannot be adjusted.

Posterior adjustable members 90, 91 are secured at their upper and lower ends to cap element 40 and back plate 54, respectively. In one embodiment, posterior adjustable members 90, 91 are secured at their upper and lower ends to cap element 40 and back plate 54 respectively by rotatable members (not shown) to allow the connections between the upper and lower ends of posterior adjustable members 90, 91 to cap element 40 and back plate 54, respectively, to pivot and rotate so that the angle of intersection between posterior adjustable members 90, 91 and cap element 40 and back plate 54 can be adjusted. Suitable rotatable members include, but are not limited to, ball and socket connections. Alternatively, only one of the connections between posterior adjustable members 90, 91 and cap element 40 or back plate 54 is rotatable, so that the other connection is fixed, i.e., the angle of intersection between posterior adjustable members 90, 91 and cap element 40 or back plate 54 cannot be adjusted.

Anterior adjustable members 80, 81 and posterior adjustable members 90, 91 may be any device known to persons skilled in the art that are capable of having their length adjusted. As shown in FIGS. 1-2, both anterior adjustable members 80, 81 and posterior adjustable members 90, 91 are formed by upper members 80A, 90A, and lower members 80B, 90B in sliding engagement with each other and held in contact with each other by bracket 82 having set screw 83. Tightening set screw 83 secures upper members 80A, 90A, and lower members 80B, 90B within bracket 82 so that no additional lengthening of anterior adjustable members 80, 81 or posterior adjustable members 90, 91 is permitted. Loosening set screw 83 releases upper members 80A, 90A, and lower members 80B, 90B from within bracket 82 so that they can sliding axially along each other thereby permitting additional lengthening of anterior adjustable members 80, 81 and posterior adjustable members 90, 91.

One or more attachment members may be included as part of trauma cervical stability device 30 so that pulleys, weights, loads, or forces can be applied to trauma cervical stability device 30 in one or more directions. For example, cap element attachment member 46 may be included as part of cap element. As shown in FIG. 1, cap element attachment member 46 is located at the upper end of posterior adjustment member 90. Additionally, breast plate attachment member 59 is located at the lower end of anterior adjustment member 80. Attachment members 46, 59 are shown in FIGS. 1-2 as hooks, however, it is to be understood that attachment members 46, 59 may be any other device capable of securing pulleys or other traction or loads to trauma cervical stability device 30. Suitable attachment members 46, 59 include snaps and belt and buckle connections.

Figure 3:
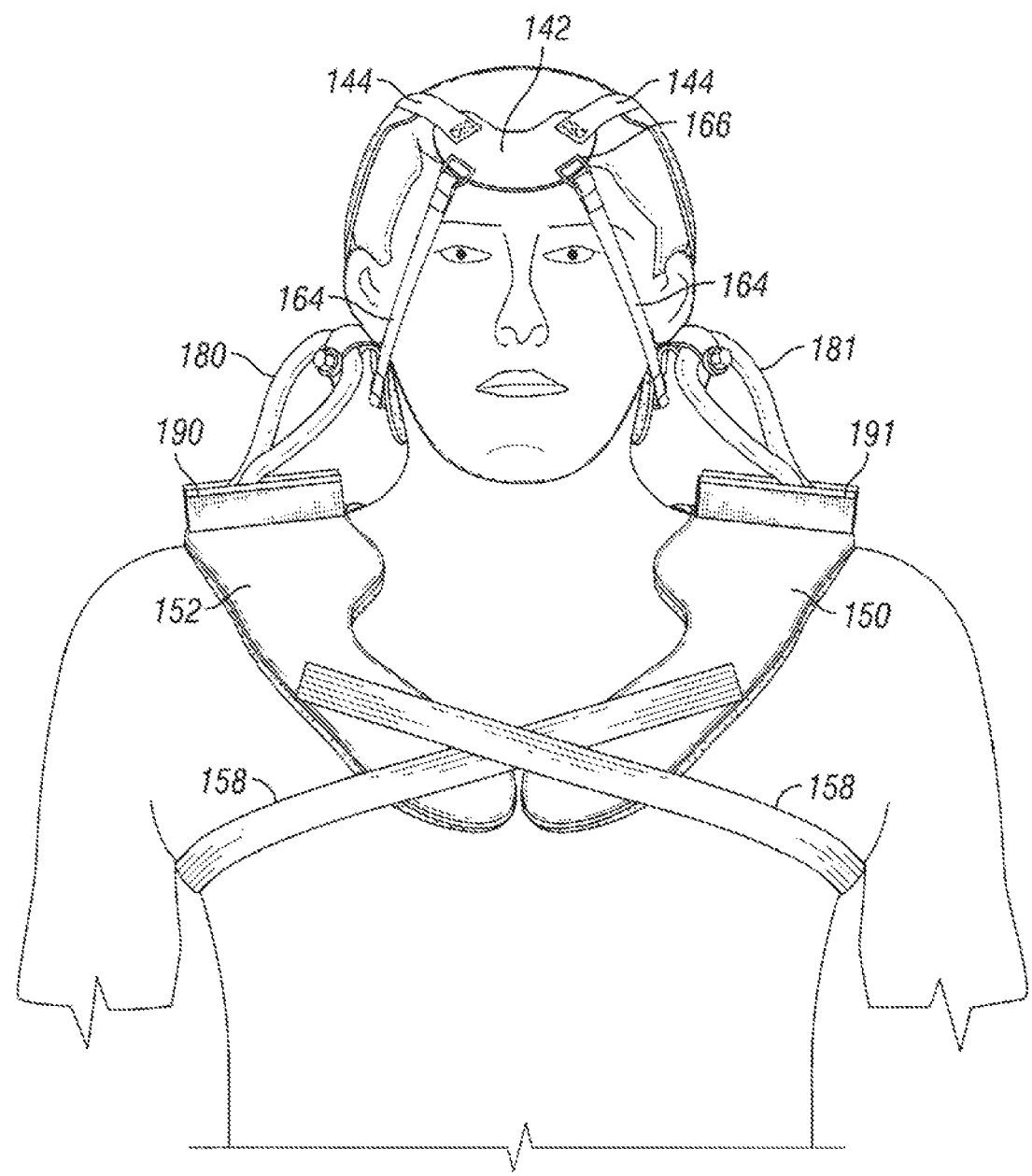
FIG. 3 is a front perspective view of another embodiment of the trauma cervical stability device disclosed herein shown secured to a patient.
Figure 4:
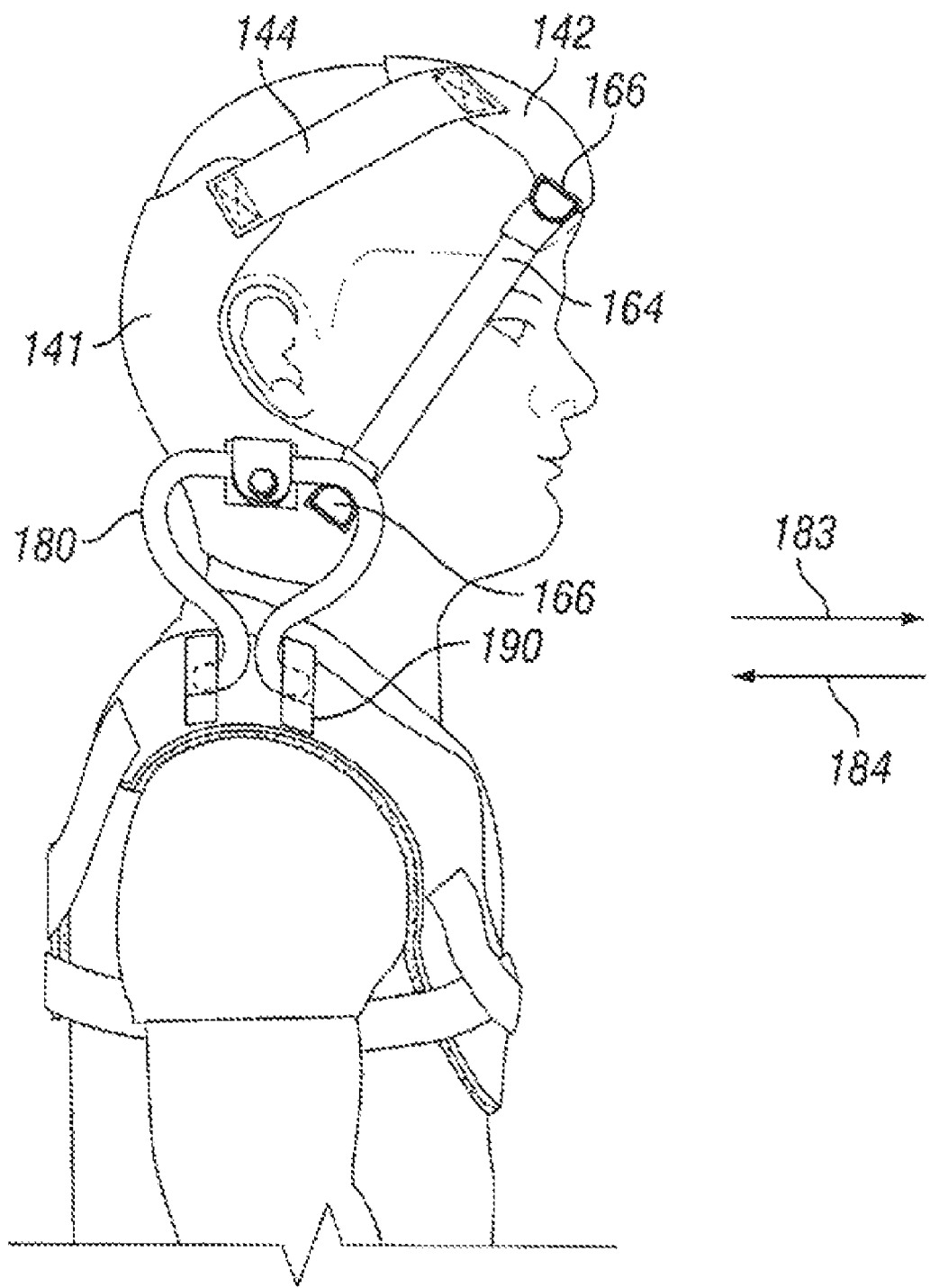
FIG. 4 is a side perspective view of the trauma cervical stability device illustrated in FIG. 3 shown secured to a patient.
Figure 5:
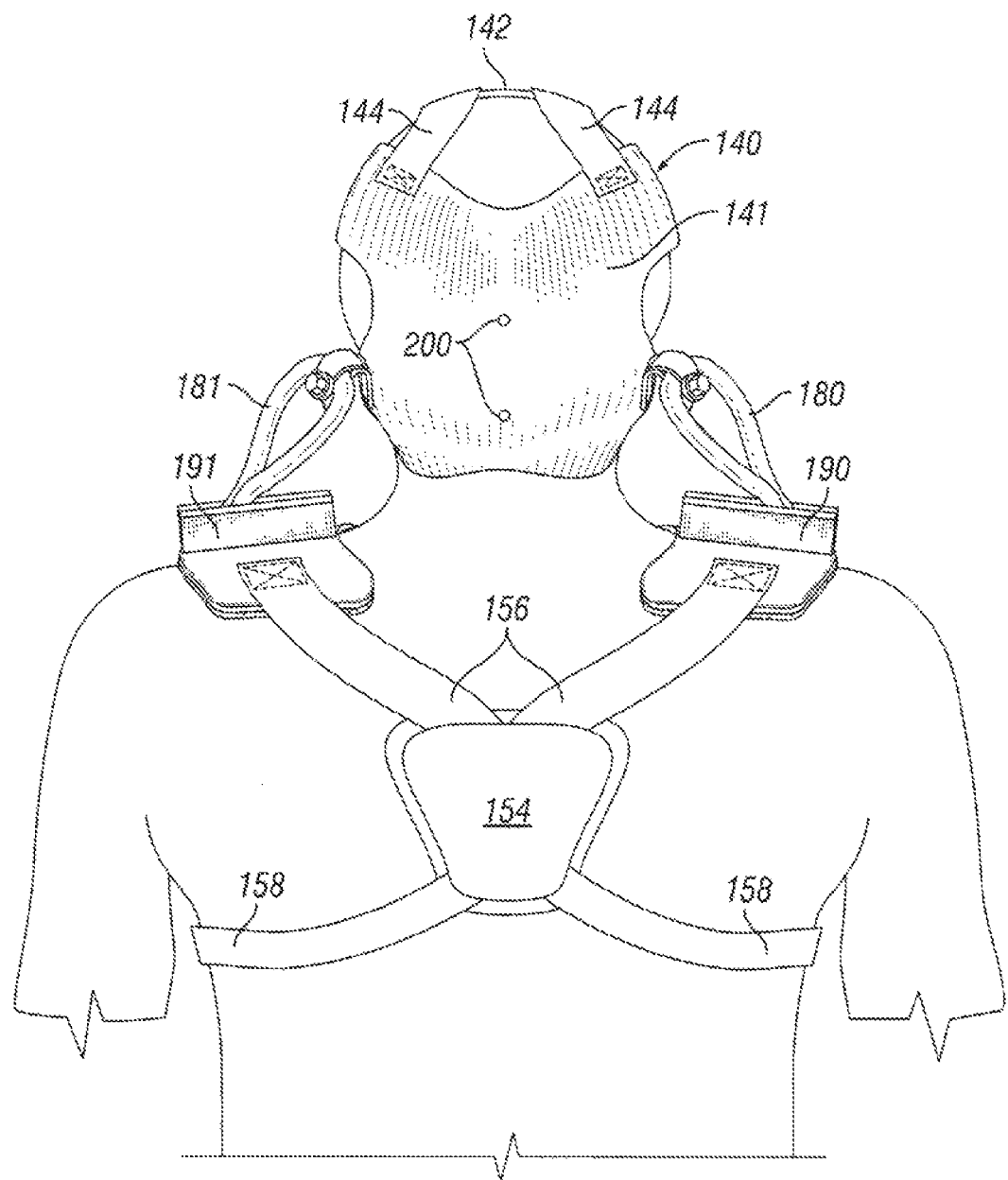
FIG. 5 is a back perspective view of the trauma cervical stability device illustrated in FIG. 3 shown secured to a patient.

Referring now to FIGS. 3-7, in another embodiment, trauma cervical stability device 130 includes cap element 140, shoulder harness 150, head straps 164, and adjustable members 180 and 181. Cap element 140 comprises two portions, posterior portion 141 and anterior portion 142. As shown in FIGS. 3-5, anterior portion 142 is position above the patient's forehead. Posterior portion 141 is connected to anterior portion 142 by cap element straps 144. Like the embodiment of FIGS. 1-2, an inner wall surface of one or both of posterior portion 141 and anterior portion 142 may be shaped for receiving the head of the patient and cap element 140 may be formed from any suitable material that provides rigidity, such as plastic materials. Additionally, a cushion material such as foam may be disposed on the inner wall surfaces of one or both of posterior portion 141 and anterior portion 142 so that inner wall surfaces of these portions of cap element 141 can conform to the contour of the patient's head. Medical gauze may also be placed between the patient's head and cap element 140 to help control bleeding from lacerations on the head. The pressure from cap element 140 can be used to help control bleeding from head lacerations.

Cap element 140 covers the posterior and crown or top portions of the head of the patient. Due to cap element 140 covering the posterior surface of the patient's head as well as a at least a portion of the crown portion of the patient's head, which, in some embodiments also includes covering a portion of the forehead of the patient, when cap element 140 is connected to shoulder harness 150 as discussed in greater detail below, a downward force is applied to the head of the patient to assist in stabilizing the head of the patient relative to the body of the patient. The term "downward force" has the same meaning as described above with respect to the embodiment of FIGS. 1-2.

Shoulder harness 150 includes front or breast plate 152 and, optionally, back plate 154. One or both of breast plate 152 and back plate 154 includes an inner wall surface having a cushion for conforming to the shape of the patient's body to support and comfort the patient's body. In one embodiment, both breast plate 152 and back plate 154 are formed from a rigid material, such as plastic, having a foam insert secured to the inner wall surface of the breast plate 152 and back plate 154. Back plate straps 156 and body straps 158 releasably and adjustably secure breast plate 152 with back plate 154 such as through the use of Velcro® pads, buckles, snaps, stitching, or other fastener members (not shown). Body straps 158 can be directly connected from the front of breast plate 152, around the body, and back to breast plate 152, such as to the portion of breast plate 152 that rests on the back of the patient's shoulders. Thus, back plate 154 is not required. Body straps 158 can be releasably and adjustably connected to front plate 152, back plate 154 or front and back plates 152, 154 to facilitate securing trauma cervical stability device 130 to the patient.

Cap element straps 144 and head straps 164 can include soft, cushioned inner wall surfaces for conforming to and/or providing comfort to, the patient's head. Both cap element straps 144 and head straps 164 may be releasably and adjustably connected to cap element 40 such as through the use of Velcro® pads, buckles, snaps, stitching, or other fastener members (not shown). Cap element straps 144 can be releasably and adjustably connected to one or both of posterior portion 141 and/or anterior portion 142 of cap element 141. Head straps 164 can be releasably and adjustably connected to cap element 140 at both ends of head straps 164. As shown in FIGS. 3-5, head straps 164 are releasably and adjustably connected to posterior portion 141 and anterior portion 142 of cap element 140 at both ends of head straps 164 by buckles 166.

Adjustable members 180, 181 are secured to cap element 140. In the embodiment of FIGS. 3-7, adjustable members 180, 181 are secured to posterior portion 141 of cap element 140. The connection between adjustable members 180, 181 and cap element 140 can comprise a rotatable member to provide a pivot point and an adjustable fastener such as a set screw or wing-nut.

Figure 6:
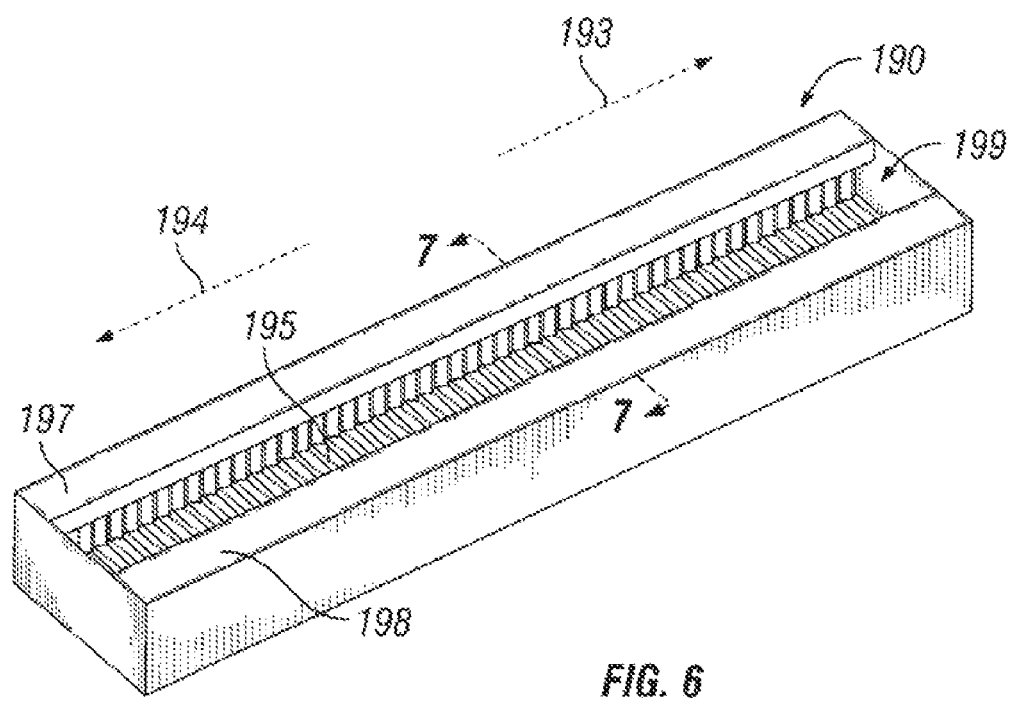
FIG. 6 is a close-up perspective view of a track for use with the trauma cervical stability device shown in FIG. 3.

The lower ends of adjustable members 180, 181 are operatively disposed in tracks 190, 191, respectively. Tracks 190, 191 permit movement of the lower ends of adjustable members 180, 181 in the direction of arrows 193 (i.e., toward the patient's head), 194 (i.e., away from the patient's head) (FIG. 6). The lower ends of adjustable members 180, 181 may be operatively associated with tracks 190, 191 in any manner known to persons of ordinary skill in the art so as to provide movement in the direction of arrows 193, 194.

Figure 7:
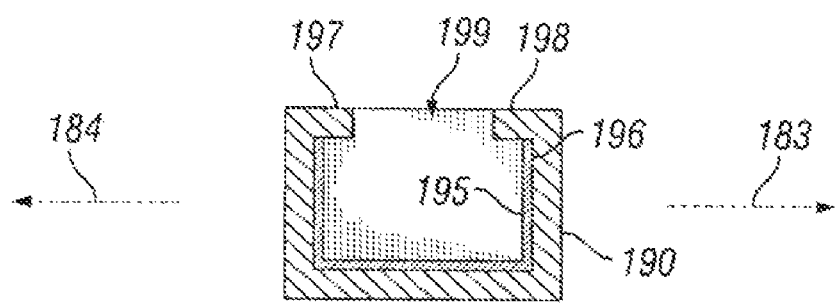
FIG. 7 is a cross-sectional view of the track shown in FIG. 6.

Referring now to FIGS. 6-7, in one particular embodiment, track 190, which for purposes of this embodiment is identical to track 191, comprises ratchet profile 195 disposed along inner wall surface 196 of tracks 190. Ratchet profile 195 permits movement of the lower ends of adjustable members 180, 181 in one direction, i.e., in the direction of arrow 193 toward the head, so that the orientation of adjustable members 180, 181 can be modified as necessary to secure trauma cervical stability device 130 to the patient. To move the adjustment members 180, 181 away from the head, each adjustment member 180, 181 or each track 190, 191 may include a release member, discussed in greater detail below, that releases adjustment members 180, 181 from ratchet profile 195, allowing movement of the lower ends of adjustment members 180, 181 within track 190, 191, respectively.

The upper side of track 191 comprises rails 197, 198 and slit 199. Rails 197, 198 restrict the lower ends of adjustable members 180, 181 from being disconnected from tracks 190, 191, respectively, while slit 199 permits the lower ends of adjustable members 180, 181 to be inserted into, and made operatively associated with, tracks 190, 191, respectively.

In this particular embodiment, the lower ends of adjustable members 180, 181 comprise a front end and a back end, each of which is outwardly biased. In other words, both front end and back ends are designed such that the front end exerts a force in the direction of arrow 183 (FIGS. 4 and 7) and the back end exerts a force in the direction of arrow 184 (FIGS. 4 and 7). Therefore, to move lower ends of adjustable members 180, 181 along tracks 190, 191 respectively, away from the head of the patient (i.e., in the direction of arrow 194), front and back ends are pinched together so as to disengage from ratchet profile 195. Thus, in this embodiment, the compression of the lower ends of adjustable members 180, 181 is the release member mentioned above. The lower ends of adjustable members 180, 181 can then be moved along the length of tracks 190, 191, respectively, in the direction away from the head to adjust the fit of trauma cervical stability device 130 to the patient.

To initially connect adjustable members 180, 181 to tracks 190, 191, adjustable members 180, 181 are disposed through slit 199 within tracks 190, 191, respectively, by turning adjustable members 180, 181 approximately 90 degrees from the orientation shown in FIGS. 3-5. After the lower ends are within tracks 190, 191, adjustable members 180, 181 are rotated 90 degrees so that the lower ends of adjustable members 180, 181 are disposed under rails 197, 199. Due to the outward biases of the front and back ends of each adjustable members 180, 181, the lower ends of adjustable members 180, 181 move outwardly and under rails 197, 199. As a result, the lower ends are retained within tracks 190, 191.

In another specific embodiment, cap element 140 includes one or more metallic studs 200 (FIG. 5). These studs are disposed substantially along the axis of the vertebra so as to provide an alignment point for imaging, e.g., X-ray, purposes. Further, attachment members (not shown) can be included as part of trauma cervical stability device 130 to provide the same functions as attachment members 46, 59 in the embodiment shown in FIGS. 1-2.

The embodiment shown in FIGS. 3-7 operates and provides the same functionality as the embodiment shown in FIGS. 1-2, with the exception of the specific methods of how trauma cervical stability device 130 is installed and adjusted on the patient. These differences are evident to persons skilled in the art based upon the discussed above with respect to the differing structures.

Although all of the structures of the trauma cervical stability devices disclosed herein can be formed out of any desired or necessary material to provide the required rigidity, plastic materials and other similar materials do not interfere with X-rays and other non-invasive imaging devices so that the trauma cervical stability devices are not required to be removed prior to imaging the patient's injury.

Trauma cervical stability devices 30, 130 may be used in any number of diagnostic techniques. In one such use, the trauma cervical stability device diagnoses the severity of damage to the neck of patient as well as diagnose whether the neck is stable prior to administering additional aid to the patient. In one embodiment, the trauma cervical stability device is secured to a patient's body and head by placing the back plate on the posterior side of the patient and the cap element on the posterior surface of the head of the patient. The breast plate is then placed on the anterior side of the patient and the one or more head straps are secured along the sides of the head of the patient and, if included, the chin strap is secured under the chin of the patient. The back plate is secured to the breast plate through the body straps and, if present, the shoulder straps.

After securing the trauma cervical stability device to the patient, each of the adjustable members are manipulated, e.g., extended, retracted, rotated, tilted, etc., to conform the trauma cervical stability device to the patient's neck and body orientation at the scene of the injury. After manipulating the adjustable member(s), the patient's neck is stabilized relative to the patient's body.

Although the patient's neck is "stabilized" relative to the body through the trauma cervical stability device, it is to be understood that the patient's neck may not be stable without the trauma cervical stability device. Additionally, the patient's neck may have sustained substantially damage that may not be evident due to the trauma cervical stability device being secured to the patient's head and body. Therefore, as discussed below, the trauma cervical stability device can be further manipulated by a physician at the hospital to determine whether the neck of the patient is stable and, if not stable, how severe the damage to the patient's neck might be.

To facilitate application of controlled traction loads to the head using the trauma cervical stability devices disclosed herein, a simple load sensing mechanism can be integrated into the articulation between adjustable members 180, 181 and cap element 140. This load-sensing articulation can provide instant feedback to a physician regarding the relative magnitude of traction that is being applied to the head by the stabilization device.

In the embodiment in which the physician determines whether the patient's neck is stable, the physician places a force or a load onto the patient's head and/or body such as by securing known weights to the attachment members of the trauma cervical stability device. The force or load caused by the weights is directed in a known direction using a pulley system. For example, the physician may place a load of 20 pounds in the upward direction parallel to the spine, i.e., pulling up on the head of a patient away from the body. If the motion between vertebrae in the spine is more than the intervertebral motion that occurs for an uninjured patient, the physician knows that the patient's cervical spine is not stable and that further diagnostic and imaging techniques, such as an MRI, are needed.

Figure 8:
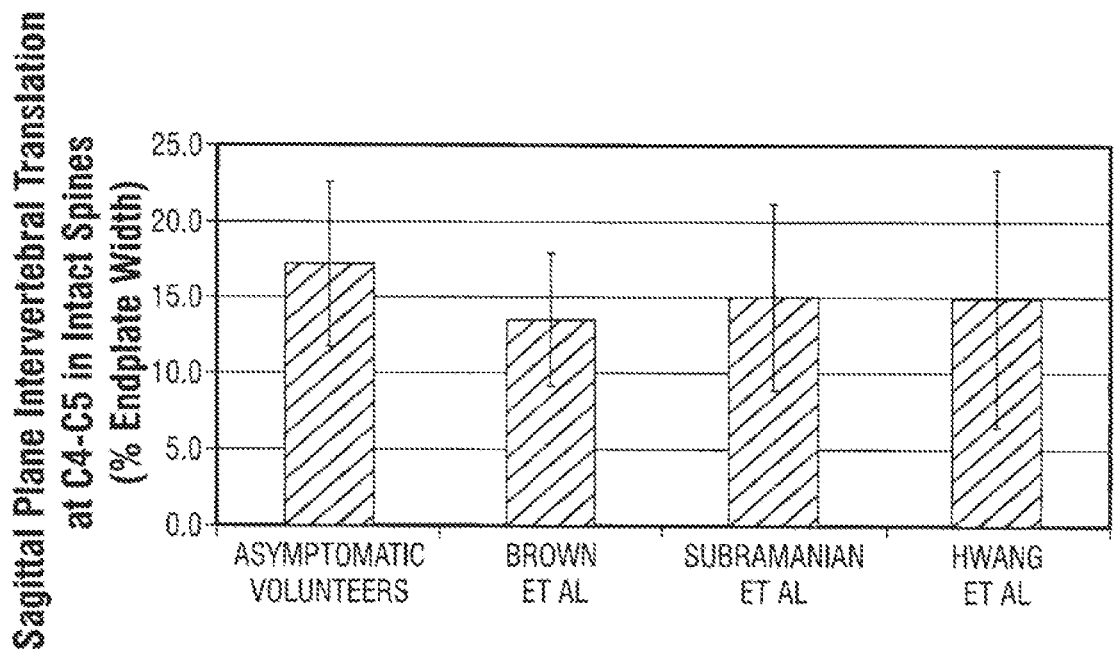
FIG. 8 is a graph showing sagittal plane intervertebral translation at C4-C5 in intact spines.

Using trauma cervical stability device 130, the inventors have completed a series of studies using whole cadavers to determine how best to diagnose injuries to the cervical spine. The whole cadaver model is a very good representation of motion live humans, since intervertebral motion in the fresh, unembalmed cadavers was statistically equivalent to motion that the authors have documented in live, asymptomatic humans. The equivalence of motion in fresh cadavers versus live humans is illustrated in FIG. 8. In FIG. 8, the data for the asymptomatic volunteers identified is from Reitman C. A., Mauro K. M., Nguyen L. et al., Intervertebral motion between flexion and extension in asymptomatic individuals; *Spine* 2004; 24:2832-43, which is hereby incorporated by reference in its entirety; the data designated "Brown, et al." is from Brown T., Reitman C. A., Nguyen L., et al., Intervertebral motion after incremental damage to the posterior structures of the cervical spine; *Spine* 2005; 30:E503-E508, which is hereby incorporated by reference in its entirety; the data designated "Subramanian et al." is from Subramanian N., Reitman C. A., Nguyen L., et al., Radiographic assessment and quantitative motion analysis of the cervical spine after serial sectioning of the anterior ligamentous structures; *Spine* 2007; 32:518-26, which is hereby incorporated by reference in its entirety; and the data designated "Hwang et al" is from Hwang H., Hipp J. A., Ben-Galim P., et al., Threshold cervical range-of-motion necessary to detect abnormal intervertebral in cervical spine radiographs; *Spine* 2007 (currently in Press), which is hereby incorporated by reference in its entirety.

Figure 9:
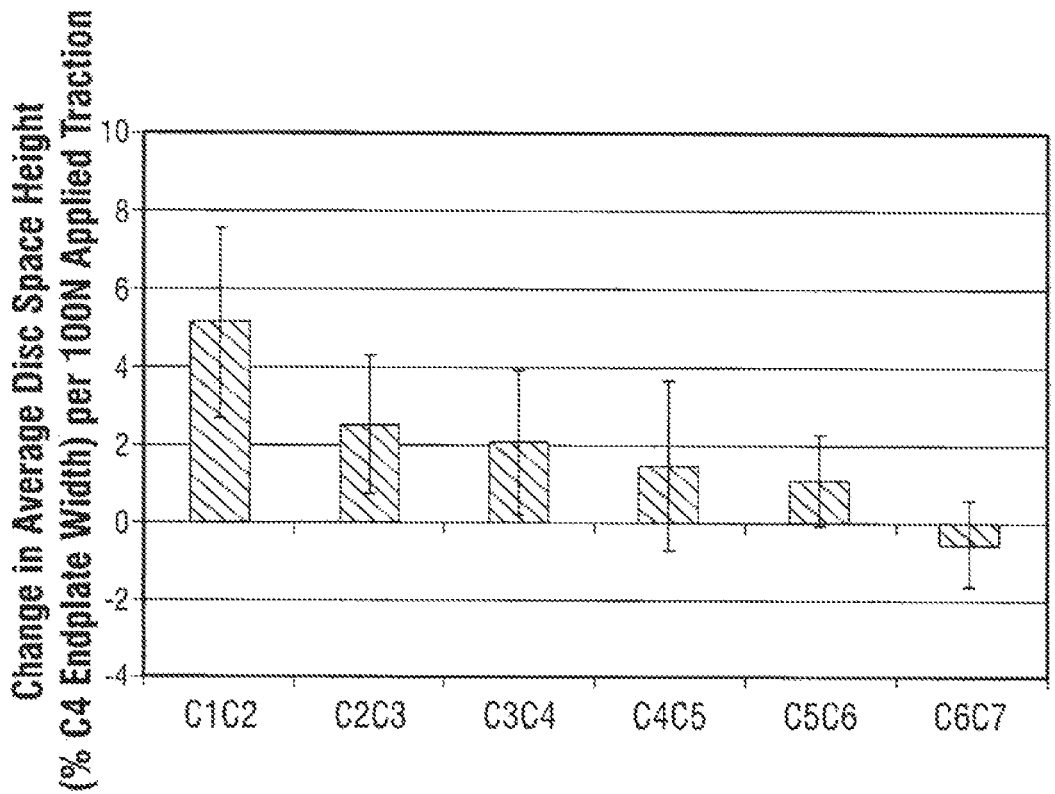
FIG. 9 is a graph showing change in average disc space height (% C4 endplate width) per 100N applied traction.

During one study, traction loads were applied to the heads of whole cadavers before and after creating injuries to the cervical spine. These experiments defined the loads that need to be applied to the head to diagnose an injury to the spine. These experiments also defined the level of loads that will not overly distract the spine yet will allow detection of damage to the spine. Results of these studies are shown in FIG. 9 which illustrates the amount of distraction that occurs in the intact cervical spine with application of axial traction, for each intervertebral level in the cervical spine.

Figure 10:
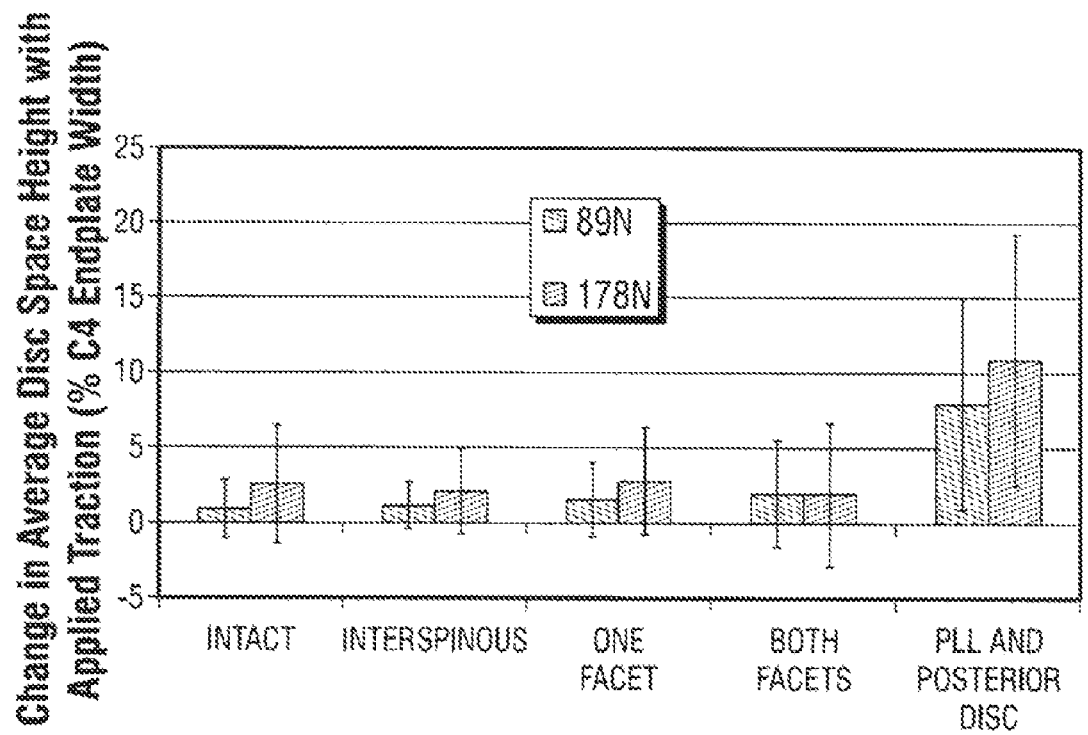
FIG. 10 is a graph showing the change in average disc space height with applied traction (% C4 endplate width).

Referring now to FIG. 10, additional results from the study using whole human cadavers are shown. As illustrated in FIG. 10, there is not a very large amount of separation between vertebrae in response to traction loads applied to the head until extensive damage is done to the spine. Statistical analysis of this data also show that a modest traction load (89 Newton=20 lbs) is actually more sensitive for diagnosing cervical injuries than a higher load (178 Newton=40 lbs).

Figure 11:
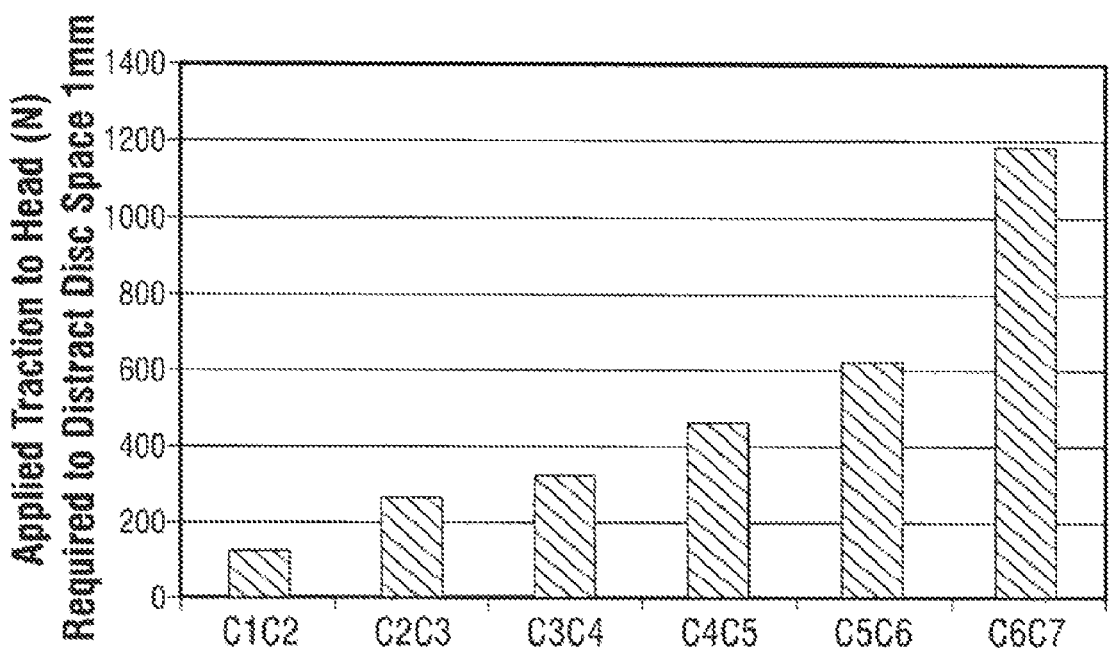
FIG. 11 is a graph showing applied traction to the head (N) required to distract disc space 1 mm.

It was further determined from the whole cadaver studies that much less traction is needed to distract the upper cervical versus lower cervical vertebrae. This observation is illustrate in FIG. 11. Using these results of these studies, physicians using trauma cervical stability device 130 can apply a number of different loads to the spine and, depending on the movement of the vertebra, can diagnose the severity of neck injury. For example, a low load would first be used to identify potential upper cervical injuries, followed by a modest load to diagnose upper or middle cervical spine injuries, followed by a higher load that would uncover injuries at any level.

In addition to the physician determining whether the neck of the patient is stable, the physician can also engage in additional diagnostic investigation as to the severity of the patient's injured and unstable neck. To do so, the physician applies known forces or loads onto the patient's head and/or body in the same manner as discussed above and then measures the distance or amount of movement between vertebrae in the spine in each direction of the force or load. Intervertebral motion is measured from x-rays or other imaging methods or devices taken before and after the load is applied. The physician then compares each of the measured intervertebral motions to motions that are indicative of certain injuries. For example, if the two vertebrae rotate away from each other when 20 pounds of force is exerted on the patient's head in the upward direction parallel to the spine, i.e., pulling up on the head of a patient away from the body, then the physician can be fairly confident that the patient's injury is extremely severe. If the two vertebrae rotate in a manner resembling motion during flexion of the head and neck, this type of rotation suggests injury to posterior structures of the spine, such as the interspinous ligaments, facets, and/or ligamentum flavum. If, during application of axial traction, the two vertebrae rotate in a manner resembling motion that occurs during extension, this type of rotation suggests damage to anterior structures, such as the anterior longitudinal ligament and/or the intervertebral disc.

Figure 12A:
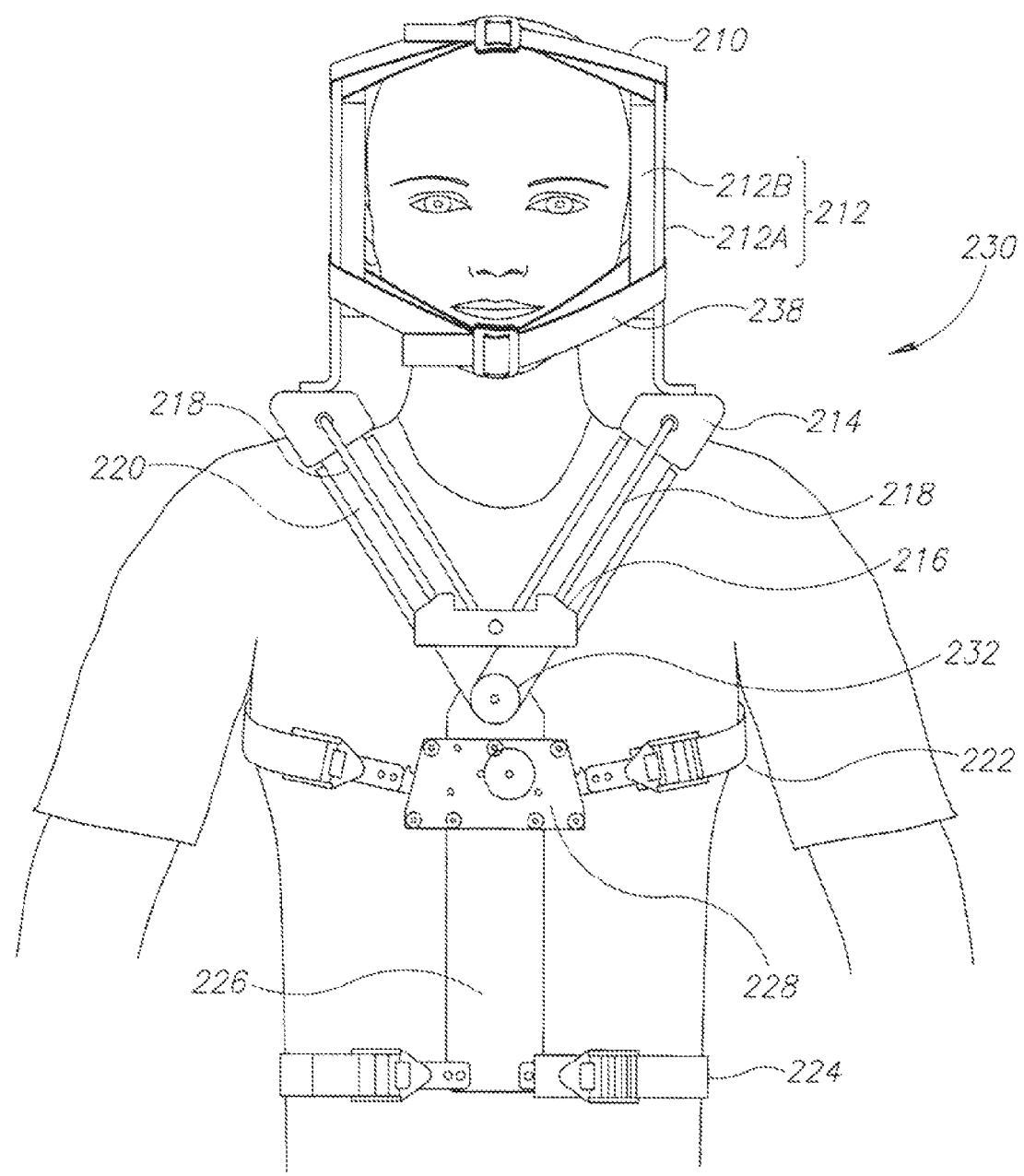
FIG. 12A is a front perspective view of another embodiment of the trauma cervical stability device disclosed herein shown secured to a patient.
Figure 12B:
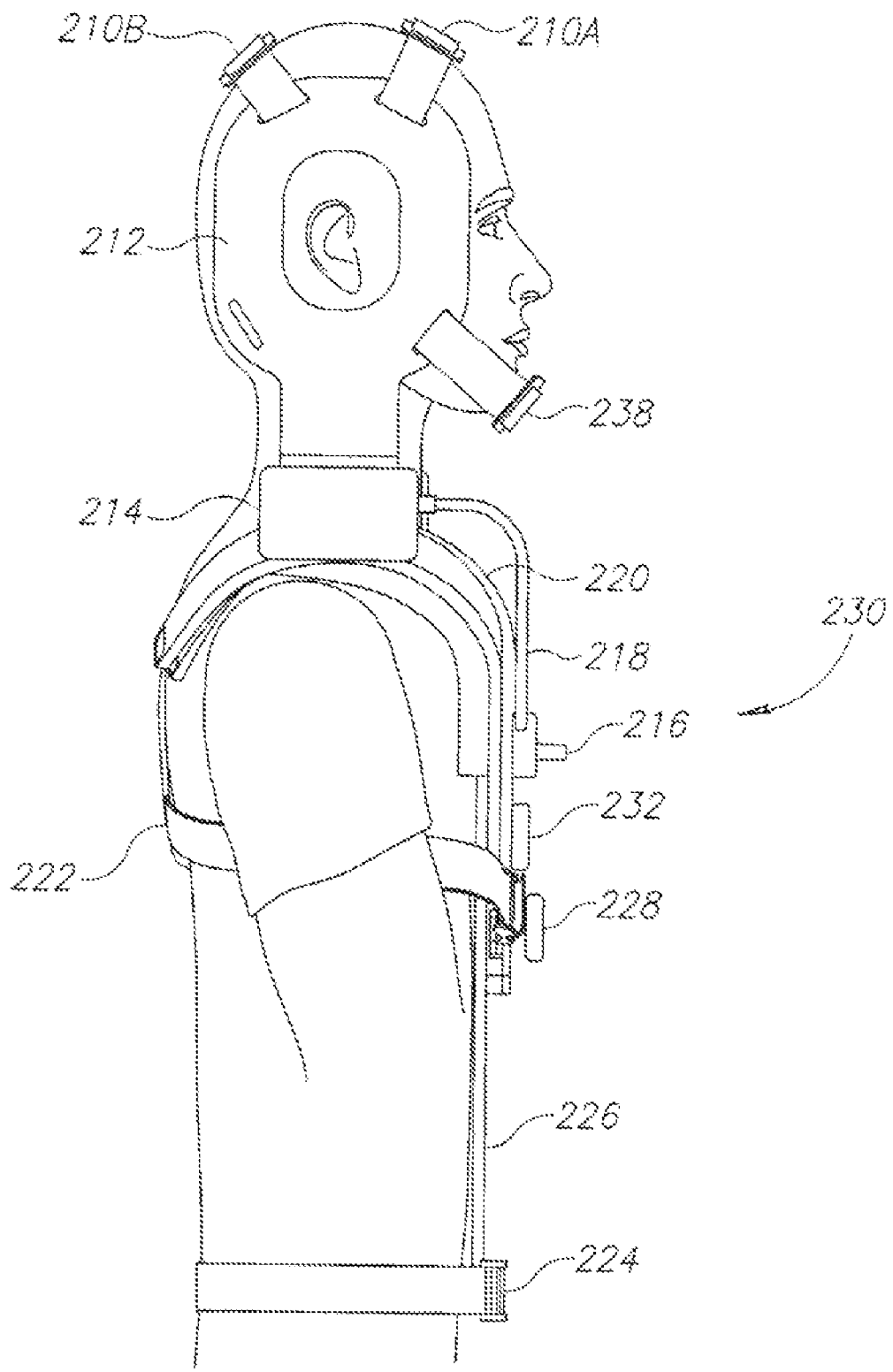
FIG. 12B is a side perspective view of the trauma cervical stability device illustrated in FIG. 12A shown secured to a patient.
Figure 12C:
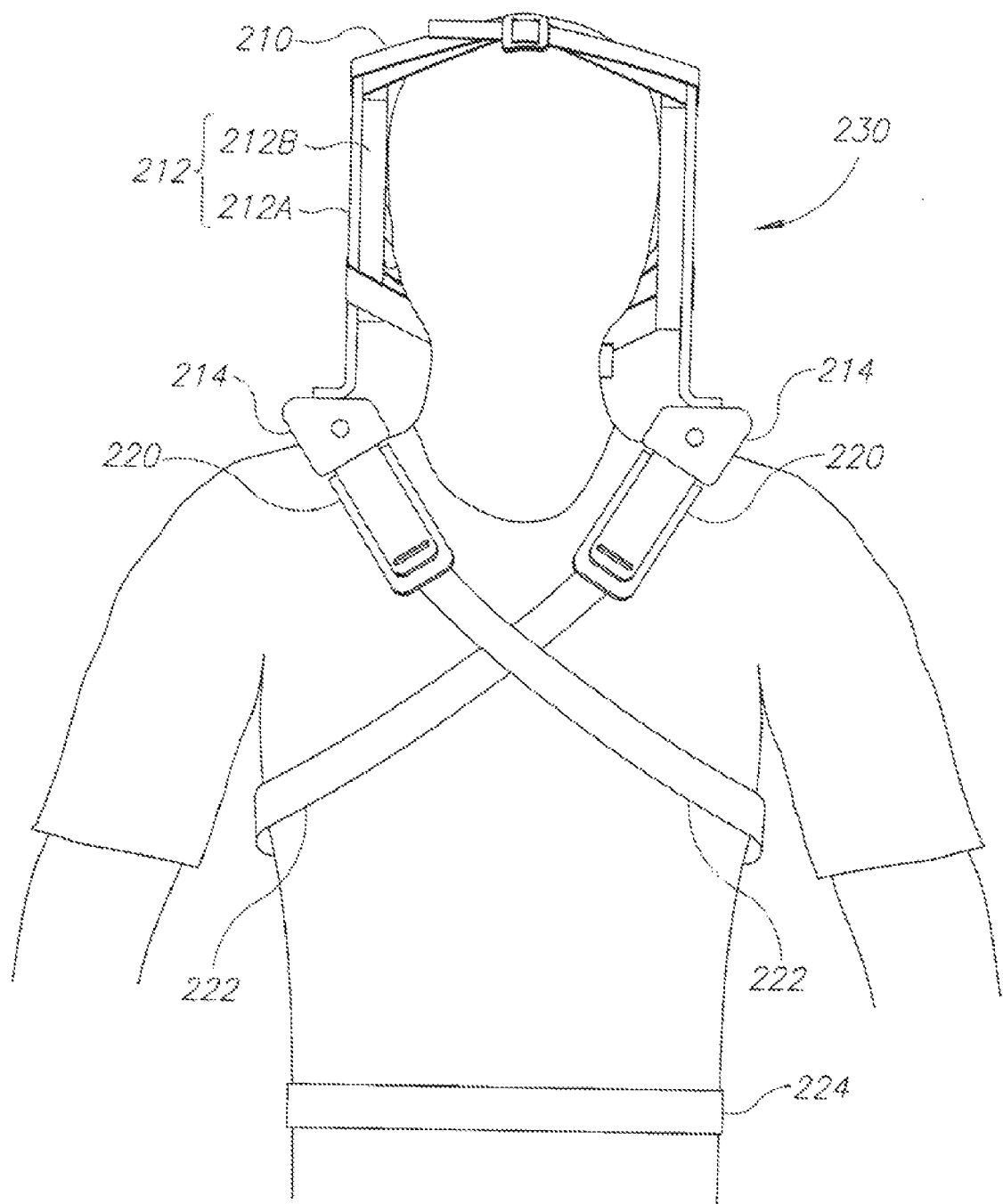
FIG. 12C is a back perspective view of the trauma cervical stability device illustrated in FIG. 12A shown secured to a patient.

Referring now to FIGS. 12A-12C, in another embodiment of the present invention, trauma cervical stability device 230 includes head straps 210, shoulder harnesses 220, lateral head elements 212, and adjustable pressure fixation elements 214.

All of the above elements of device 230 as well as the additional elements, such as connectors and fasteners, discussed below may be made of suitable materials, such as plastics, metals, and fabrics. However, without intending to limit the invention, they are preferably made of materials other than metals so that they can be compatible with magnetic resonance imaging (MRI) and computerized tomography (CT) scans. It is envisioned that a patient wearing device 230 may have to undergo MRI and CT scans without removing device 230.

In this embodiment "upper" or "top" means that part of an element, member, etc. closest to the crown of the head while "lower" or "bottom" means that part of an element, member, etc. furthest from the crown of the head. Similarly, "distal", "outer", "outermost", or like terms mean that portion of an element, member, etc. that is most distant from the patient's body while "proximal", "inner", "innermost" or like terms mean that portion of an element, member, etc. that is closest or adjacent to the patient's body. As is anatomical convention, "dorsal" refers to the back of the body or torso that is the side closest to the spinal cord, while "ventral" refers to the side of the body or torso closest to the abdomen.

Head straps 210 comprise two straps, an anterior head strap 210A and a posterior head strap 210B. As shown in FIGS. 12A-12C, anterior head strap 210A is positioned adjacent to the patient's forehead on the anterior surface of the head while posterior head strap 210B is positioned on the crown surface of the head. Head straps 210A and 210B may be releasably and adjustably connected to lateral head elements 212, the latter discussed herein below. This connection may be effected by using, for example, Velcro® pads, snaps or buckles.

Both anterior and posterior head straps 210A and 210B, respectively, may be formed of two parts which may be adjustably and releasably secured to each other with a connecting element, such as, but without limiting the invention, buckles, snaps or Velcro® pads.

In alternate embodiments, each of head straps 210A and 210B may be formed as a single piece; each end of single piece straps 210A and 210B may be adjustably and releasably secured to a different lateral head element 212, the latter element discussed immediately below.

Head straps 210 may be constructed of Velcro®, plastics, such as nylon, cloth, and rubber or other elastomeric materials and may include soft, cushioned inner wall surfaces for conforming to and/or providing comfort to, the patient's head.

Each side of the head is covered by a lateral head element 212, substantially centered over the ears of the trauma patient. Lateral head element 212 may be constructed so that the regions adjacent to the ears of the patient are absent making for greater comfort of the patient. As noted above, each of anterior and posterior head straps 210A and 210B are adjustably and releasably secured to both lateral head elements 212.

Lateral head elements 212 comprise two layers: a soft layer 212B, typically, but without limiting the invention, constructed from foam or sponge. Soft layer 212B is disposed on the inside surface of lateral head elements 212, that is, the surface disposed adjacent to the patient's head. A plastic layer 212A is disposed over soft layer 212B, the plastic layer formed of a rigid plastic, such as polycarbonate, acrylonitrile/butadiene/styrene, or polyvinyl chloride. Soft layer 212B and plastic layer 212A may be releasably attached to each other.

The design of device 230 allows for placement of head straps 210 and lateral head elements 212 on the patient with a minimum of undesirable movement of the head.

A chin strap 238 may be adjustably and releasably secured to the lower portion of each lateral head element 212 and positioned substantially across the chin of the patient. Chin strap 238 may be constructed of Velcro®, polymers such as nylon, cloth, and rubber or other elastomeric materials.

The bottom of lateral head elements 212 are secured to a pair of vacuum pillow members 214, herein also designated as pressure fixation elements, using any suitable connector elements. Each lateral head element is fastened to a different one of the pair of vacuum pillow members 214. Vacuum pillow members 214 are typically formed of any soft but strong fabric and filled with any hard particulate material, such as, but without intending to limit the invention, polycarbonate or polyethylene beads. Without limiting the invention, connectors for connecting vacuum pillow members 214 to lateral head elements 212 may include Velcro® pads, screws and glue.

When device 230 is placed on the trauma patient, vacuum pillow members 214, also designated herein as pressure fixation elements 214, are in their non-rigid and non-evacuated mode. At this stage, they are somewhat firm and stiff but not fully rigid and hard and can not in themselves at this stage be used as support members. They are easily positionable next to the neck of the patient, substantially at the junction of the neck and shoulder that is on the trapezius muscle. As the final stage of applying device 230 after all the straps of the device have been adjusted and releasably secured and after shoulder harnesses 220, discussed immediately below, have been properly positioned, pillow members 214 are evacuated with a suitable pump. This causes pillow members 214 to firm up and harden considerably allowing them to be used to support the head and neck of the patient. They prevent movement of the head and neck of the patient in relation to the torso and are intended to maintain the head and neck in the position they were found at the site of the injury. The position of the head in relation to the torso at the site of the injury is designated herein as their "instant relative disposition".

Device 230 includes shoulder harnesses 220. Each vacuum pillow member 214 is disposed and secured to a different shoulder harness 220. Methods for securing pillows 214 to shoulder harnesses 220 include, but are not limited to, Velcro® pads and screws. Harnesses 220 extend substantially from the region of the patient's sternum and reach over the patient's shoulders to the dorsal side of the torso. Shoulder harnesses 220 may comprise a foam/sponge layer disposed as the inner surface of the harness, adjacent to the trauma patient's torso. A rigid plastic layer is disposed over the foam/sponge layer and forms the outer layer of shoulder harnesses 220. The rigid layer conforms to the human anatomy while the foam/sponge layer facilitates fitting of the device to the specific patient.

Disposed between shoulder harnesses 220 on the ventral side of the torso is a vacuum valve member 216. This member comprises a one-way valve, typically a plastic one-way valve, which allows the ambient to be in controllable fluid communication with vacuum pillow members 214 via conduits 218. Conduits 218 may be constructed from any suitable flexible polymer such as, but without attempting to limit the invention, polyurethane, fluoropolymers, polyvinyl polymers and silicon.

It should readily be understood that in some embodiments there may be two vacuum valve members 216 each in operative connection with a different conduit 218.

When device 230 is to be removed, valve member 216 is opened and air flows from the ambient via conduits 218 to pillow members 214 allowing them to return from their second mode of operation, their rigid mode, to their first mode of operation, their non-rigid mode, wherein they are firm but not fully rigid. After returning vacuum pillow members 214 to their first mode, the upper part of device 230, that is head straps 210, lateral head elements 212, and chin straps 238, may be removed from the trauma patient.

Shoulder harnesses straps 222 may be adjustably and releasably secured to shoulder harness 220, typically, but not necessarily, on the dorsal side of the shoulders. Shoulder harness straps 222 then may be wrapped around the patient's torso to connect to a shoulder harness strap tightening member 228, which is disposed on breast plate 226, the latter element discussed below. The shoulder harness strap tightening member 228, typically, but without attempting to limit the invention, may be a ratchet element. Shoulder harness strap tightening member 228 tightens and holds shoulder harness straps 222, and, concomitantly, device 230, tightly in place.

Shoulder harness straps 222 may be releasably and adjustably secured to shoulder harness 220 and shoulder harness strap tightening member 228 using any of many types of connectors, such as Velcro® pads, buckles, snaps, stitching, or other fastener members (not shown). Buckles, snaps or any other fastener members used with device 230 may be made of any suitable materials. However, without intending to limit the invention, the fastening members are preferably made of materials other than metals so as not to interfere with MRI and/or CT scans as discussed above.

An angle fixation element 232 is in mechanical communication with and disposed on the lower end of shoulder harnesses 220. Angle fixation element 232 is tightened once the proper angle between the shoulder harnesses 220 is attained. This angle inter alia is a function of the thickness of the neck of the patient. Tightening the angle fixation element fixes the position of, and angle between, shoulder harnesses 220 and applying a vacuum to vacuum pillows 214 causes lateral head elements 212, head straps 210 and vacuum pillow members 214 to become fixed and stabilized as they are brought taut against the head and shoulders of the trauma patient.

It should be evident that when shoulder harnesses 220 and vacuum pillow members 214 are properly positioned, there is no undesirable movement of the patient's head relative to his body. The disposition of the head to the torso is the instant relative disposition defined above. Because of the design of device 230, there is no downward or partially downward or upwards or partially upwards force applied to the head of the patient causing possible irreversible damage to the spine.

Shoulder harnesses 220 positioned in their fixed configuration form a "V" of different angles allowing the device to be used for patients of different neck widths. When device 230 is to be fixed on the patient, lateral head elements 212 and vacuum pillow members 214 should be positioned as close to the neck as possible. This reduces head movement when the patient's shoulders are moved.

Breast plate 226 extends from approximately the region of the sternum down to approximately the waist on the ventral side of the patient's torso. As noted above, disposed on breast plate 226 is shoulder harness strap tightening member 228 and angle fixation member 232. Breast plate 226 may be constructed from a soft material such as foam or sponge on top of which is disposed a rigid plastic material. The sponge and rigid plastic layers may be releasably attached to one another. The sponge layer, or other similar soft layer, may be conformed to the shape of the patient's body to support and comfort the patient's body.

Optionally, at least one waist strap 224 may be used; these may be adjustably and releasably fastened to the bottom of breast plate 226 with any adjustable and releasable connectors known to persons skilled in the art. Waist straps 224 may be tied around the waist region of the patient to provide greater stability of device 230 after positioning it on the torso of the patient.

As with shoulder harness straps 222, waist straps 224 may be secured using any fastening connectors known to those skilled in the art, such as Velcro® pads, buckles, snaps, stitching, or other fastener members (not shown).

It is envisioned that an elongated element (not shown) such as an elongated rod with, for example, a receiving member, such as a hook on one of its ends, may be used to engage and pass shoulder harness straps 222 underneath an immobilized patient. The patient, for example, could be lying on his back. Utilizing the elongated element, the harness straps 222 may be brought to a position where they can be secured to shoulder harness strap tightening member 228. Similarly, waist straps 224 may be brought from underneath an immobilized patient to the front of the patient's torso to releasably and adjustably be secured to the lower end of breast plate 226.

The advantage of the embodiment shown in FIGS. 12A-12C is that unlike previous embodiments, this embodiment is usable with, and mountable on, a patient when the patient is in a prone, or any other, position. Only minimal movement of the patient is necessary to mount device 230 on the patient. Unlike prior art devices or the other embodiments of the present invention, device 230 of this embodiment need not be applied only from above, i.e. from the direction of the head of the patient. It may be applied from above as well as from the ventral or lateral sides of the patient. Additionally, device 230 is intended to fix the head relative to the torso of the patient in its instant relative disposition.

The embodiment shown in FIGS. 12A-12C is usable in an operating room, in an emergency room and even while the patient is undergoing CT or MRI scans. The device shown in FIGS. 12A-12C may be applied to a trauma patient even in confined spaces.

Device 230 shown in, and discussed in conjunction with, FIGS. 12A-12C is intended to fix the head in its position relative to the torso as initially found by first responders, that is, in its instant relative disposition. The head can be essentially vertical i.e. perpendicular to the plane formed by the shoulders of the patient, that plane substantially at a right angle (perpendicular) to the neck. As noted above, regardless of the position of the head, the head is fixed by device 230 in the position in which it is found. As a result of using vacuum pillow members 214 there is no need to straighten the head before fixation of the device as is done today. Device 230 applies no direct forces to the head as long as the patient is not moved in any way. After the device is properly applied, it prevents movement of the head relative to the body. Only while the patient is moving does the device apply forces to the head. When the head is immobilized, the forces are only static forces.

Recent medical trauma literature implies that a cervical collar is only needed in situations where unstable cervical spine injury such as "internal decapitation" or OCI "occipitocervical dissociative injuries" are suspected. "Internal decapitation" and OCI are unstable cervical injuries which are characterized predominantly by damage to the connecting soft tissues of the neck (ligaments, facet capsules, discs, etc.) leading to internal separation and dissociation between vertebral segments of the spine. This mechanism may occur without any external indications and requires hospital imaging facilities, such as fine cut CT scans and MRI, to diagnose.

Internal decapitation and OCI result in unstable C-spine injuries. Once the C-spine becomes unstable, the vertebrae are free to move one on top of the other and/or one around the other in all six planes of freedom of motion in three dimensions. These movements include bending, rotation, twisting, shearing, compression, flexion and extension. Neurological injury may occur due to full incision, partial incision and ischemia of the spinal cord.

There is no way to determine in the field if a patient is suffering from internal decapitation, OCI or other pathologies which leads to an unstable C-spine injury. Therefore, all patients who are suspected of these kinds of injuries must be fitted with a proper C-spine immobilizer per current trauma paradigms.

The current gold standard is the C-spine collar (CSC). It is being placed on almost every patient involved in traumatic incidents. The collar stays in its proper location by applying tension to the neck. It does this by press fitting between the base of the head and mandible to the shoulders. In effect application of CSC is achieved by pressing the upper part of the collar to the mandible and base of the skull and base of the head, while the bottom part of the collar presses onto the patient's shoulders.

When applied on patients without an unstable C-spine injury, the CSC will not cause separation of vertebral segments, as in injured unstable necks. Still the stretch and pressure associated with CSC have been well documented to cause undesirable side effects, such as pressure ulcers, elevated intracranial pressures, obstructed CSF (cerebrospinal fluid) or venous flow, and difficult intubations. However, devastating damage to patients has been documented when CSC are applied on patients with an unstable C-spine injury; the collar will cause extension of the spinal cord that may lead to neurological injuries, according to the mechanism described above.

In practice, applying a CSC on patients who need it will actually worsen their injuries. The only way to prevent additional injury to the patient is by using a device, such as device 230, which does not apply forces on the head and/or against the shoulders.

Mounting device 230 on a patient is effected by employing the following steps:

1. placing shoulder harnesses 220 on the torso of the patient;

2. adjusting shoulder harnesses 220 and vacuum pillow members 214 for patient neck size and then adjusting the angle formed between the shoulder harnesses 220 by using, and locking, angle fixation element 232;

3. bringing shoulder harness straps 222 to the ventral side of the patient, connecting them to shoulder harness strap tightening member 228, and using tightening member 228 to tighten the shoulder harness straps 222 around the patient;

4. bringing waist straps 224 around the body, connecting them to breast plate 226 and tightening them around the patient's waist;

5. adjusting and releasably securing the head straps 210 and chin strap 238; and 6. applying a vacuum to the vacuum pillow members 214 to cause the pillows to become rigid and enabling them to support the head and neck region of the patient.

In what is described herein with respect to FIGS. 12A-12C and the discussion thereof, it has been assumed that the patient is found lying on his back, or substantially on his back, and that the cervical stability device 230 is positioned on the patient when he is in that instant relative disposition. However, it is also contemplated that the device 230 may be placed on the patient when he is lying face down without having to turn him. In such a case, it should be readily understandable that breast plate 226 is positioned on the back, substantially along the spine, shoulder harnesses 220 are positioned on the back and reach slightly over the shoulder to the ventral side of the body, and valve member 216 also lies on the dorsal side of body. In effect, in such a case, all the elements and members of the device shown and discussed as being positioned on the ventral side of the torso may be positioned on the dorsal side of the body. This is possible because lateral head elements 212 have multiple degrees of freedom relative to shoulder harnesses 220 prior to their being fixed in place by vacuum pillow members 214. Accordingly, it should be understood that the specification, figures and claims cover the situations where the patient is lying face up, face down or any intermediate position when device 230 is being positioned on the patient. Further, it should be understood that in the claims any orientation designated is not necessarily the literal orientation but dependent on the instant relative disposition of the patient.

In summary, device 230 substantially differs from CSC and other modes of cervical spine immobilization for in field trauma injury patients. Device 230 differs in concept due to the following features:

a) This device differs from traditional cervical collars in that it is designed to accomplish a novel type of cervical stabilization termed "in situ stabilization", also referred to herein as "instant relative disposition" stabilization. This is a radical departure from the concept achieved by current cervical collars namely "in line stabilization" in which the neck is forced into a predetermined straight alignment. Essentially, current collars force the head and neck of the patient to be moved until they are in line with the longitudinal axis of the body. These manipulations of the injured patient and spine may be detrimental and sometimes lead to catastrophic neurological damage.

The cervical stabilization device with its versatile adjustability allows for fixation of the head and neck to the torso in the position that they were found in the field, i.e. "in situ stabilization"

b) This device's adjustability also allows for different head, neck and body shapes and sizes to be treated without underfixation or over-distraction.

c) Another concept in which this device conceptually differs from collars is in its ability to "grasp" the head and the torso accordingly in order to allow true stabilization.

d) The vacuum pillows connecting the head grasping mechanism to the torso grasping mechanism of the device allow for initial adjustability and positioning. Once air is withdrawn from the pillows they become rigid resulting in their fixation of the head and neck relative to the torso.

e) The described device differs in concept from cervical collars in that it does not physically touch the neck of the patient and does not exert forces upon the neck. Therefore the described device acts as a protective guarding device that does not require applying forces around or directly onto the neck.

It is to be understood that the invention is not limited to the exact details of construction, operation, exact materials, or embodiments shown and described, as modifications and equivalents will be apparent to one skilled in the art. For example, the head straps may be a single strap that extends from one side of the cap element, passes through a slot on the top of the cap element, and extends to the other side of the cap element where it is releasably and adjustably connected to the cap element. Moreover, the tracks may not include a ratchet profile, but instead include slots or holes into which the lower ends of the adjustable elements are inserted. Accordingly, the invention is therefore to be limited only by the scope of the appended claims.

What is claimed is:

1. A trauma cervical stability device for use on a patient having a torso and a head connected by a neck, the torso having dorsal and ventral sides and the head having an anterior surface and a crown surface, wherein the head has an instant relative disposition to the torso, the trauma cervical stability device comprising:
a pair of shoulder harnesses adapted to be placed onto the ventral side of the torso such that each harness partially extends over a different shoulder;
a pair of lateral head elements, each lateral head element constructed to be positionable on the head independently of the other and each associated with a different one of said shoulder harnesses and having multiple degrees of freedom of movement relative thereto, said pair of lateral head elements adapted for positioning on opposing sides of the head; and
a pair of adjustable pressure fixation elements, each associated with a different one of said pair of shoulder harnesses and secured to the bottom of a different one of said lateral head elements, each said fixation element adapted for positioning at the junction of the neck and the shoulders of the patient and operable in a first and second mode of operation,
wherein, in the first mode of operation said fixation elements are non-rigid and do not restrict movement of said lateral head elements, and in the second mode of operation, they are rigid so as to restrict movement of said lateral head elements, thereby to fix the head in relation to the torso in their instant relative disposition.

2. The trauma cervical stability device of claim 1, further comprising:
a pair of shoulder harness straps releasably secured to said shoulder harnesses at the dorsal side of the shoulders;
a breast plate for positioning on the ventral side of the torso; and
a shoulder harness strap tightening element disposed on said breast plate, said tightening member operative to adjustably and reversibly tighten said shoulder harness straps when said straps extend from said shoulder harnesses around the torso to said breast plate.

3. The trauma cervical stability device of claim 2, wherein said shoulder harness strap tightening element is selected from a group consisting of a ratchet member, an adjustable bearing member and an adjustable strap.

4. The trauma cervical stability device of claim 2, wherein the breast plate is formed of two layers, a soft layer and a rigid layer, the soft layer positioned on a surface of the rigid layer proximal to the torso.

5. The trauma cervical stability device of claim 2, further comprising an angle fixation element disposed on and in mechanical communication with said breast plate and said pair of shoulder harnesses, said angle fixation element adjusting and locking the angle between said pair of shoulder harnesses after they are positioned on the patient.

6. The trauma cervical stability device of claim 2, further comprising a waist strap releasably and adjustably fastened to the lower end of said breast plate and disposed so that it fits around the torso of the patient.

7. The trauma cervical stability device of claim 1, further comprising a one-way valve member connected via plastic conduits to said pressure fixation elements, said valve member having an open and a closed state, wherein in the closed state said pressure fixation elements when under vacuum retain their vacuum allowing them to support the head and neck of the patient in their instant relative disposition and when in the open state air flows from the ambient through said valve to the pressure fixation elements reducing their rigidity and their ability to support the head and neck of the patient.

8. A trauma cervical stability device of claim 7, wherein each of said pressure fixation elements include at least one aperture through which a vacuum may be applied and where when a vacuum is applied to said fixation elements said elements become rigid allowing them to support and fix the head and neck of the patient relative to the torso in their instant relative disposition.

9. A trauma cervical stability device of claim 7, wherein said pressure fixation elements are vacuum pillows.

10. The trauma cervical stability device of claim 1, further including two adjustable head straps that are disposed on said lateral head elements and extend over the head of the patient at its crown surface and its anterior surface from one lateral head element to the other.

11. A trauma cervical stability device of claim 10, wherein said lateral head elements and said head straps are configured to allow their positioning on the head of the patient irrespective of the instant relative disposition of the head and torso of the patient.

12. The trauma cervical stability device of claim 1, further comprising a chin strap releasably and adjustably connected to said pair of lateral head elements positioned so that said chin strap fits over the chin of the patient.

13. The trauma cervical stability device of claim 1, wherein said lateral head elements are formed of two layers, a soft layer and a rigid layer, the soft layer positioned on a surface of the rigid layer adjacent to the head.

14. The trauma cervical stability device of claim 1, wherein said shoulder harnesses are formed of two layers, a soft layer and a rigid layer, the soft layer positioned on a surface of the rigid layer adjacent to the torso.

15. A trauma cervical stability device for use on a patient having a torso and a head connected by a neck, the torso having dorsal and ventral sides and the head having an anterior surface and a crown surface, wherein the head has an instant relative disposition to the torso, the trauma cervical stability device comprising:
a pair of shoulder harnesses adapted to be placed onto the ventral side of the torso such that each harness partially extends over a different shoulder;
a pair of lateral head elements each associated with a different one of said shoulder harnesses and having multiple degrees of freedom of movement relative thereto, said pair of lateral head elements adapted for positioning on opposing sides of the head;
a pair of adjustable pressure fixation elements, each associated with a different one of said pair of shoulder harnesses and secured to a different one of said lateral head elements, each said fixation element adapted for positioning at the junction of the neck and the shoulders of the patient and operable in a first and second mode of operation, wherein, in the first mode of operation said fixation elements are non-rigid and do not restrict movement of said lateral head elements, and in the second mode of operation, they are rigid so as to restrict movement of said lateral head elements; and
a one-way valve member connected via plastic conduits to said pressure fixation elements, said valve member having an open and a closed state, wherein when in the open state air flows from the ambient through said valve member to the pressure fixation elements reducing their rigidity and their ability to support the head and neck of the patient, and when in the closed state said pressure fixation elements when under vacuum retain their vacuum allowing them to support the head and neck of the patient, thereby to fix the head in relation to the torso in their instant relative disposition.

16. A trauma cervical stability device of claim 15, wherein each of said pressure fixation elements include at least one aperture through which a vacuum may be applied and where when a vacuum is applied to said fixation elements said elements become rigid allowing them to support and fix the head and neck of the patient relative to the torso in their instant relative disposition.

17. A trauma cervical stability device of claim 15, wherein said pressure fixation elements are vacuum pillows.

18. A trauma cervical stability device for use on a patient having a torso and a head connected by a neck, the torso having dorsal and ventral sides and the head having an anterior surface and a crown surface, wherein the head has an instant relative disposition to the torso, the trauma cervical stability device comprising:

a pair of shoulder harnesses adapted to be placed onto the ventral side of the torso such that each harness partially extends over a different shoulder;

a pair of lateral head elements each associated with a different one of said shoulder harnesses and having multiple degrees of freedom of movement relative thereto, said pair of lateral head elements adapted for positioning on opposing sides of the head; and a pair of adjustable pressure fixation elements, each associated with a different one of said pair of shoulder harnesses and secured to a different one of said lateral head elements, each said fixation element adapted for positioning at the junction of the neck and the shoulders of the patient and operable in a first and second mode of operation, said pressure fixation elements being vacuum activated elements, wherein, in the first mode of operation said fixation elements are non-rigid and do not restrict movement of said lateral head elements, and in the second mode of operation, they are rigid so as to restrict movement of said lateral head elements, thereby to fix the head in relation to the torso in their instant relative disposition.

* * * * *